(12) United States Patent
Schilthuizen et al.

(10) Patent No.: US 9,033,908 B2
(45) Date of Patent: May 19, 2015

(54) DEVICE FOR THE REMOVAL OF TOXIC SUBSTANCES FROM BLOOD

(75) Inventors: Stephanus Franciscus Schilthuizen, Berkel-Enschot (NL); Lawrence Fabian Batenburg, Eindhoven (NL); Frank Simonis, Oirschot (NL); Franky Flory Vercauteren, Eindhoven (NL)

(73) Assignee: Nederlandse Organisatie voor toegepast—natuurwetenschappelijk onderzoek TNO, Delft (NL)

( * ) Notice: Subject to any disclaimer, the term of this patent is extended or adjusted under 35 U.S.C. 154(b) by 1110 days.

(21) Appl. No.: 12/520,005

(22) PCT Filed: Dec. 19, 2007

(86) PCT No.: PCT/NL2007/050669
§ 371 (c)(1),
(2), (4) Date: Nov. 2, 2009

(87) PCT Pub. No.: WO2008/075951
PCT Pub. Date: Jun. 26, 2008

(65) Prior Publication Data
US 2010/0100027 A1 Apr. 22, 2010

(30) Foreign Application Priority Data

| Dec. 21, 2006 | (EP) | 06077295 |
| Jan. 24, 2007 | (EP) | 07101127 |
| Mar. 5, 2007 | (EP) | 07103515 |
| May 4, 2007 | (EP) | 07107504 |

(51) Int. Cl.
*A61M 1/14* (2006.01)
*A61M 1/36* (2006.01)
(Continued)

(52) U.S. Cl.
CPC ........... *A61M 1/3679* (2013.01); *A61M 1/1696* (2013.01); *A61M 1/3472* (2013.01); *A61M 2209/088* (2013.01)

(58) Field of Classification Search
CPC ........... A61M 1/14; A61M 1/16; A61M 1/36; B01D 69/02
USPC ........... 604/5.01, 6.01–6.04, 6.09, 6.11, 6.13, 604/6.14, 6.16; 210/645, 646, 767, 777
See application file for complete search history.

(56) References Cited

U.S. PATENT DOCUMENTS 4,013,564 A 3/1977 Nose
6,589,549 B2 * 7/2003 Shih et al. ............ 424/426

(Continued)

FOREIGN PATENT DOCUMENTS

DE 2741888 A1 3/1979
DE 4239442 A1 6/1994
(Continued)

*Primary Examiner* — Melanie Hand
(74) *Attorney, Agent, or Firm* — Mannava & Kang, P.C.

(57) ABSTRACT

The present invention relates to a device for the removal of toxic substances from dialysate fluid, blood or blood plasma, said device comprising i) a sorption-filter (E) for removing toxins, toxic solutes, toxic small and middle-sized molecules and protein bound toxins from the dialysate fluid, blood or bloodplasma, said sorption filter comprising a nanostructured material, a porous polymer matrix or a combination of the two, ii) an inlet (4) for entry of dialysate fluid, blood or blood plasma into said device, iii) an outlet (5) for the removal of purified dialysate fluid, blood or blood plasma from said device, and iv) a conduit connecting said inlet with said outlet and holding said sorption filter such that said dialysate fluid, blood or blood plasma is forced through said sorption filter.

31 Claims, 9 Drawing Sheets

(51) Int. Cl.
*A61M 1/16* (2006.01)
*A61M 1/34* (2006.01)

(56) References Cited

U.S. PATENT DOCUMENTS

| | | |
|---|---|---|
| 6,977,171 B1 | 12/2005 | Dennis et al. |
| 2004/0118779 A1 | 6/2004 | Rawson et al. |
| 2004/0228829 A1 | 11/2004 | Roberts et al. |

FOREIGN PATENT DOCUMENTS

| | | |
|---|---|---|
| EP | 1745808 A1 | 1/2007 |
| GB | 1406133 | 9/1975 |
| GB | 2000150 A | 1/1979 |
| GB | 1552248 | 9/1979 |
| JP | 49-10595 | 1/1974 |
| WO | WO95/29731 A1 | 11/1995 |

* cited by examiner

DEVICE FOR THE REMOVAL OF TOXIC SUBSTANCES FROM BLOOD

This application is a national phase application of, and claims priority to, PCT/NL2007/050669, filed Dec. 19, 2007, which claims priority to European Application Nos. 06077295.1 filed Dec. 21, 2006, 07101127.4 filed Jan. 24, 2007, 07103515.8 filed Mar. 5, 2007 and 07107504.8 filed May 4, 2007, the disclosures of which are incorporated herein by reference.

FIELD OF THE INVENTION

The present invention is in the field of artificial kidneys and dialysis systems. The invention relates to a device for the removal of toxic substances from blood from a patient, to methods of removing toxic substances from blood using the inventive device and to filter pads suitable for use in said device and in hemodialysis and peritoneal dialysis systems.

BACKGROUND OF THE INVENTION

Hemodialysis (HD) and peritoneal dialyis (PD) are methods of removing toxic substances (impurities or wastes) from the blood when the kidneys are unable to do so sufficiently. Dialysis is most frequently used for patients who have kidney failure, but may also be used to quickly remove drugs or poisons in acute situations. This technique can be life saving in people with acute or chronic kidney failure. Best known is hemodialysis, which works by circulating the blood along special filters outside the body in a dialysis machine. Here, the blood flows across a semi-permeable membrane (the dialyser or filter), on the other side of which flows a dialysis fluid in a counter-current direction to the blood flow. The dialysing membrane allows passage of substances below a certain molecular cut-off. By diffusion the concentration of these substances will end up being the same on both sides of the membrane. The dialysis fluid removes the toxins from the blood and is generally discarded as waste dialysate. The chemical imbalances and impurities of the blood are being brought back in minimal balance and the blood is then returned to the body. The efficacy of hemodialysis is 10-15%, which means that 10-15% of the toxins are being removed from the blood. Typically, most patients undergo hemodialysis for three sessions every week. Each session lasts normally 3-4 hours. This is very inconvenient, and the physical and social side effects of dialysis to the patients are a great concern.

The efficacy of peritoneal dialysis is even lower. In PD, a soft catheter is used to fill the abdomen with a dialysis solution that generally contains dextrose and bicarbonate. The peritoneal membrane, which lines the walls of the abdominal cavity, allows waste products and extra fluid to pass from the blood into the dialysis solution. The saturated dialysis solution is then drained from the body and is discarded. The exchange process of filling and draining takes about 30 to 40 minutes.

In order to provide for portable dialysis devices, that will allow patients to engage in normal daily activities, artificial kidneys have been developed. Essentially there are two types of artificial kidneys.

In one form, the principle of the artificial kidney consists of extracting urea and other more toxic middle molecules from blood by dialysis and regeneration of the dialysate by means of an adsorbent, usually activated carbon. In the case of a system based on such a dialysis kidney machine, a key aspect resides in regenerating the dialysis fluid when the latter is to be recycled into the dialyser. Dialysis kidney machines that can be encountered in the prior art include for instance those described in GB 1 406 133, and US 2003/0097086. GB 1 406 133 discloses an artificial kidney of the recycle type having an improved adsorbent comprising activated carbon and alumina. US 2003/0097086 discloses a portable dialysis device comprising dialyzers connected in series that utilize dialysate, and further comprising a plurality of contoured sorbent devices, which are connected in series and are for regenerating the spent dialysate. As adsorption materials for regeneration of the spent dialysate, activated charcoal, urease, zirconium phosphate, hydrous zirconium oxide and/or activated carbon are provided.

In another form, the principle of the artificial kidney may be based on ultrafiltration, or hemofiltration, using appropriate membranes, wherein large molecules including blood cells are retained in the retentate on the filter, and the toxic substances are collected in the (ultra)filtrate. During hemofiltration, a patient's blood is passed through a set of tubing (a filtration circuit) via a machine to a semipermeable membrane (the filter) where waste products and water are removed. Replacement fluid is added and the blood is returned to the patient. In a similar fashion to dialysis, hemofiltration involves the movement of solutes across a semipermeable membrane. However, the membrane used in hemofiltration is far more porous than that used in hemodialysis, and no dialysate is used-instead a positive hydrostatic pressure drives water and solutes across the filter membrane where they are drained away as filtrate. An isotonic replacement fluid is added to the resultant filtered blood to replace fluid volume and valuable electrolytes. This is then returned to the patient. Thus, in the case of ultrafiltration, a key aspect resides in separating the urea from the other components in the ultrafiltrate such as salts which have also passed through the membrane but which must be reincorporated into the blood in order to maintain the electrolyte composition thereof substantially constant.

A combination of the two systems described above has also been proposed. Shettigar and Reul (Artif. Organs (1982) 6:17-22), for instance, disclose a system for simultaneous filtration of blood using a hemofilter and dialysis against its purified filtrate, wherein the filtrate is purified by a multi-adsorption system consisting of charcoal for removal of urea and a cation exchanger.

Intermediate systems, i.e. systems that perform no ultrafiltration, yet which adsorb toxic substances directly from the blood have also been proposed. US 2004/0147900 discloses a cartridge for treating medical or biological fluid, in particular blood, consisting of a compartmentalized container, wherein each compartment contains adsorbing particles. The adsorption materials proposed are essentially those disclosed in US 2003/0097086 described above, and thus may effectively remove urea from blood.

As noted above, the adsorbent for regenerating the dialysate is usually activated carbon. However other adsorbents have been proposed for the removal of substances from dialysis fluids or ultrafiltrate. U.S. Pat. No. 3,874,907, for instance, discloses microcapsules consisting essentially of a crosslinked polymer containing sulphonic acid groups and coated with a polymer containing quaternary ammonium groups, for use in an artificial kidney. Examples of the sulphonated polymer include sulphonated styrene/divinyl benzene copolymer and examples of the coating polymer include those obtained by polymerization of for instance vinyldimethylamine monomers. Shimizu et al. (Nippon Kagaku Kaishi (1985), (6), 1278-84) described a chemisorbent composition for the removal of urea from dialysis fluid or hemofiltrate for use in an artificial kidney. The chemisorbent is based on dialdehyde starch (DAS)-urease conjugates and 4,4'-diamidinodiphenylmethane (DADPM).

In conclusion, the prior art discloses both dialysing and ultrafiltration devices, wherein various substances may be used as sorbents.

The problem with the system of the prior art is that however, that they are still too large due to limited sorption capacity of the materials, or not efficient or both in order to allow small, desk-top sized or wearable dialysing and ultrafiltration systems.

It is an object of the present invention to overcome the problems associated with the devices of the prior art and to provide a compact and efficient sorption-filter system for use in hemodialysis and peritoneal dialysis systems and in an artificial kidney.

SUMMARY OF THE INVENTION

This problem is solved according to the invention by providing a small sorption-filter device for the removal of toxic substances from hemodialysis and peritoneal fluids, allowing very little dialysate volume and thereby allowing a small, desk-top size or wearable hemodialysis or peritoneal dialysis system. This problem can also be solved according to the invention by providing a small device for the removal of toxic substances directly from the blood from a patient, comprising of a hemofilter for separating patient blood plasma from patient blood cells and a sorption-filter for removing toxic ionic solutes, toxic small- and middle-sized molecules and protein bound toxins from the patient's blood plasma.

Said sorption-filter comprises an absorbing, adsorption, ion-exchange and/or surface crystallisation material with very small nano sized particles having a large specific surface area in combination with a high chemical surface activity like nanoclays, nanocrystalline hydrotalcites, nanoporous silica's, nanoporous or layered alumina silicates (like zeolites), nanoporous metal oxides and metal hydroxides, metal organic frameworks, zeolite imidazolate frameworks, nano-sized and/or activated graphite, cyclo-dextrines, crystallisation seeds, a highly porous matrix material with again a large specific surface area, with tunable porocity and a high specific chemical activity like carboxymethyl cellulose and like a biopolymer such as oxidized starch modified with functional groups for specific absorption or combinations thereof.

In a first aspect, the present invention provides a device for the removal of toxic substances from dialysate fluid, blood or blood plasma, said device comprising:
i) a sorption-filter for removing toxins, small and middle-sized molecules from the dialysate fluid, blood or bloodplasma, said sorption filter comprising a sorbent material selected from the group consisting of:
  a nanostructured sorption material;
  a porous polymer matrix, wherein the pores in said matrix are of a size that allows the entry into said matrix of toxic substances sought to be removed from said liquid and/or preventing the entry into said matrix of substances not sought to be removed from said liquid; and
  a nanostructured sorption material captured in a porous polymer matrix, wherein the pores in said porous polymer matrix are of a size that allows the entry into said matrix of substances sought to be removed from said liquid while preventing the escape of said nanostructured sorption material and/or preventing the entry into said matrix of substances not sought to be removed from said liquid.

ii) an inlet for entry of dialysate fluid, blood or blood plasma into said device,
iii) an outlet for the removal of purified dialysate fluid, blood or blood plasma from said device, and
iv) a conduit connecting said inlet with said outlet and holding said sorption filter such that said dialysate fluid, blood or blood plasma must pass through said sorption filter when flowing from said inlet to said outlet.

In a preferred embodiment of a device of the present invention said nanostructured sorption material is selected from the group consisting of
  a) nanoparticles or nanocrystalline materials, preferably metal silicates such as nanoclays, preferably an exfoliated nanoclay, metal hydroxides, preferably layered double hydroxides like a nano-hydrotalcite or pure metaloxide nanoparticles;
  b) nanoporous materials, preferable selected from zeolites, mesoporous systems and metal organic frameworks;
  c) nanocomposites;
  d) nanofibers,
  e) any combination of the above.

In another preferred embodiment of a device of the present invention said porous polymer matrix is based on a cross-linked polymer and/or a charged polymer and/or a polymer modified with specific functional groups for specific absorption.

In yet another preferred embodiment said polymer is a biopolymer selected from carbohydrates and proteins.

In still another preferred embodiment said carbohydrate is an oxidized crosslinked starch.

In still another preferred embodiment said carbohydrate is a carboxymethyl cellulose.

In another preferred embodiment the pores in said matrix are of a size that prevents the entry into said matrix of albumin and other useful blood components such as transferrin and vitamin B12

In another preferred embodiment said toxic substances are selected from potassium, phosphate, urea, uric acid, ammonia, creatinine, beta2-microglobulin ($\beta$2M), and albumin-bound toxins such as paramino hyppuric acid and bilirubin.

In a further preferred embodiment said sorbent material further comprises means for supplementing said dialysate fluid and/or said (purified) blood plasma with at least one substance selected from the group consisting of vitamins, minerals, anticoagulants, anti microbial agents and medicaments.

In a still preferred embodiment said sorption filter is provided in the form of a filter pad (pouch) comprising a sorbent material as defined in any one of claims 1-8, and further optionally comprising a hemofilter.

In another preferred embodiment the sorbent material is provided in the form of dried granules having a mean size over the range 250 microns to 1500 microns based on the size in dried form.

In yet another preferred embodiment said device further comprises means for supplementing said dialysate fluid and/or said (purified) blood plasma with at least one substance selected from the group consisting of vitamins, minerals, anticoagulants, anti microbial agents and other medicaments.

In yet another preferred embodiment said sorption filter is part of a hemodialysis or peritoneal dialysis system in order to improve the absorption capacity of the dialysis fluid, to minimize the dialysate fluid volume and/or to minimize the dimensions of the dialysate system, thereby allowing the dialysate system to be wearable.

In yet another preferred embodiment said dialysis system is a wearable dialysis system.

In a preferred embodiment said device comprises a pump for pumping said dialysate fluid, blood or blood plasma from said inlet to said outlet.

In a preferred embodiment said sorption-filter is combined with a hemofilter system in order to form an artifical kidney device for the removal of toxic substances from the blood from a patient, comprising a hemofilter for separating patient blood plasma from patient blood cells, and a sorption-filter for removing toxins, toxic small- and middle-sized molecules and protein bound toxins from the patient blood plasma and optionally to supplement the blood with at least one substance selected from the group consisting of vitamins, minerals, anticoagulants, anti microbial agents and other medicaments.

In a preferred embodiment said artficial kidney system is a system that improves the clearance performance of existing hemodialysis and peritoneal systems.

In a preferred embodiment said artficial kidney system is a system that eliminates the use of a dialysate fluid in an existing hemodialysis system.

In a preferred embodiment said artificial kidney system is a wearable device.

In a further preferred embodiment said hemofilter comprises at least one inlet for receiving blood from a patient, and at least one outlet for recovery of patient blood plasma.

In a further preferred embodiment said hemofilter comprises at least a further outlet for recovery of patient blood cells.

In yet a further preferred embodiment said sorption-filter comprises an inlet for receiving patient blood plasma exiting said hemofilter, and at least one outlet for recovery of purified blood plasma.

In another preferred embodiment said sorption-filter is combined with a permeable envelop to form a filter pad comprising an envelop surrounding a filter pad contents, wherein the envelop of said pad comprises a permeable membrane and the contents of said pad comprise said sorbent material.

In another preferred embodiment said hemofilter and said sorption-filter are combined to form a filter pad comprising an envelop surrounding a filter pad contents, wherein the envelope of said pad comprises said hemofilter, and the contents of said pad comprise said sorbent material.

In another preferred embodiment said device further comprises ion exchange systems.

In another preferred embodiment said device further comprises surface crystallisation systems.

In another aspect, the present invention provides a filter pad comprising a sorbent material as defined herein and adapted for being held in the conduit fluidly connecting the inlet and outlet of the device of the present invention.

In a preferred embodiment of such a filter pad, the sorbent material is the material as defined under c) as defined above (nanostructured material captured in porous polymer matrix), wherein the sorbent material is provided in the form of dried granules having a mean size over the range 250 microns to 1500 microns based on the size in dried form, and said filter pad further comprising a permeable envelop containing said sorbent material.

In another aspect, the present invention provides a method for removing toxic substances from dialysate fluid, blood or blood plasma, comprising using a device according to the present invention, optionally in combination with a filter pad according to the present invention.

DETAILED DESCRIPTION OF THE INVENTION

Figure 1:
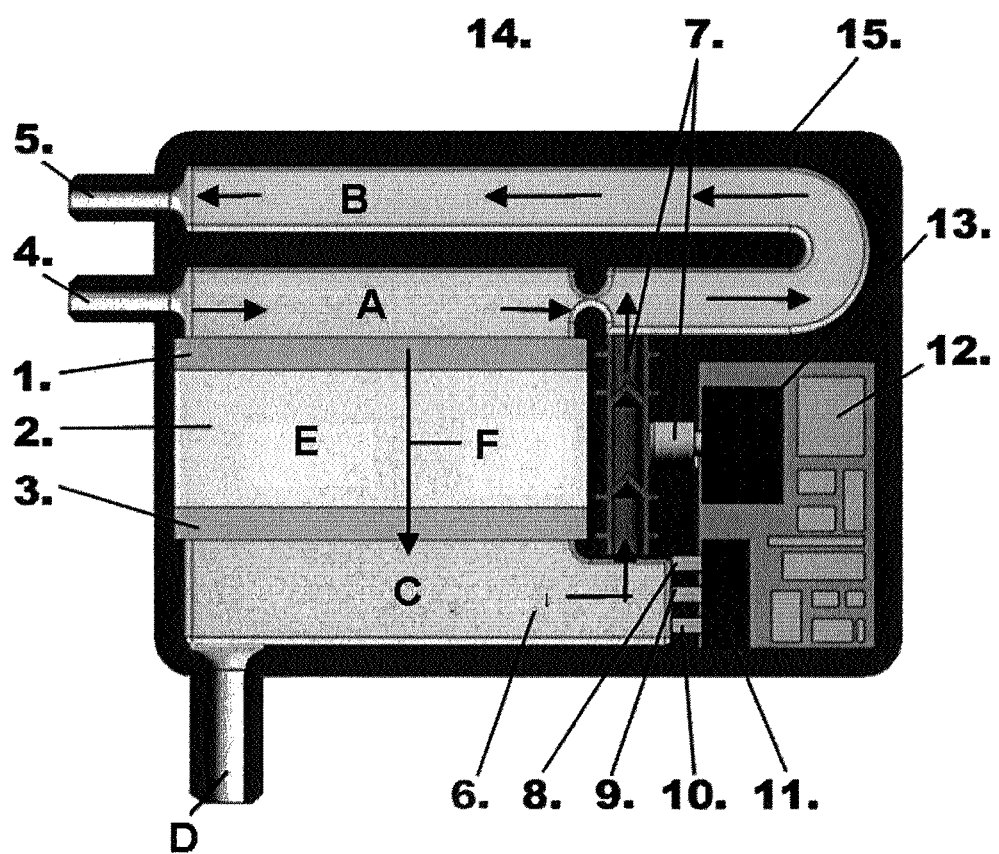
FIG. 1 shows a cross-sectional presentation of a device according to the invention.

The term "sorption" as used herein, refers to both adsorption and absorption. Adsorption is a process that occurs when a gas or liquid or solute (called adsorbate) accumulates on the surface of a solid or more rarely a liquid (adsorbent), forming a molecular or atomic film (adsorbate). It is different from absorption, where a substance diffuses into a liquid or solid to form a "solution". The term sorption encompasses both processes, while desorption is the reverse process.

The term "small-sized molecules", as used herein, refers to molecules with a molecular weight lower than 500 Da, such as uric acid, urea, guanidine, ADMA, creatinine.

The term "middle-sized molecules", as used herein, refers to molecules with a molecular weight between 500 Da and 5000 Da, such as end products from peptides and lipids, amines, amino acids, protein bound compounds, cytokines, leptins, microglobulins and some hormones.

The term "nanoporous materials" refers to materials having pores that are by definition roughly in the nanometre range, that is between $1\times10^{-7}$ and $0.2\times10^{-9}$ m and includes reference to the 3 categories set out by IUPAC of microporous materials (such as zeolites) having pore sizes of 0.2-2 nm; mesoporous materials having pore sizes of 2-50 nm; and macroporous materials having pore sizes of 50-1000 nm.

The term "ionic solutes", as used herein, refers to components such as phosphates, sulphates, carbon hydrates, chlorides, ammonia, potassium, calcium, sodium.

"Nano sized" as used herein, refers to a size of approximately 1-1000 nm, more preferably 1-100 nm.

The Purification Device Holding the Sorption Filter

A device of the present invention can take the form of a sorption-filter package that is placed in the dialysis fluid system of a hemodialysis or peritoneal dialysis system enabling the removal of toxins from the dialysis fluid. The sorption filter continuously purifies the dialysate fluid, keeping the toxin concentration in the dialysis fluid low, resulting in an improvement of the hemodialysis and peritoneal dialysis efficiency, typically with 100%, and reduces the consumption of dialysis fluid needed dramatically, ideally down to 1-10 litres. An additional and optional function of the sorption filter is to release ingredients for supplementing of the blood such as calcium, vitamin A, C and B12, anti-coagulation agents, anti microbial agents, minerals, specific medicaments etc. This option will simplify the operation of existing hemodialysis and peritoneal dialysis systems and will reduce the chance on occurring infections in the peritoneal dialysis system.

A device of the present invention can take the form of wearable peritoneal dialysis system wherein the sorption-filter package is placed in a wearable peritoneal dialysis system. Due to the continuous filtering of the sorption filter, the volume of dialysate fluid can be reduced to typically 1-2 litres. The wearable peritoneal dialysis device comprises a tubular access system to the abdominal cavity and a unit comprising a fluid pump, power, sensors, electronic control, a facility to place and replace said sorption-filter package, typically on a daily basis and a system to dispose off excess water. An additional and optional function of the sorption filter is to release ingredients for supplementing the blood, such as calcium, vitamin A, anti-coagulation agents, anti microbial agents, minerals, specific medicaments etc. This option will enhance the operation of the peritoneal dialysis system and will reduce the chance on occurring infections.

A device of the present invention can take the form of wearable hemodialysis system wherein the sorption-filter package is placed in a wearable hemodialysis system. Thanks to the continuous filtering of the sorption filter, the volume of dialysate fluid can be reduced to typically 1-2 litres. The wearable hemodialysis device comprises a vascular access tubing system and a unit comprising a small hemofilter system, fluid pump, power, sensors, electronic control, a facility to place and replace said sorption-filter package, typically on a daily basis, and a system to dispose off excess water. An additional and optional function of the sorption filter is to release ingredients for supplementing the blood such as calcium, vitamin A, anti-coagulation agents, anti microbial agents, minerals, specific medicaments etc. This option will simplify the operation of the hemodialysis system and will reduce the chance on occurring infections.

Figure 2:
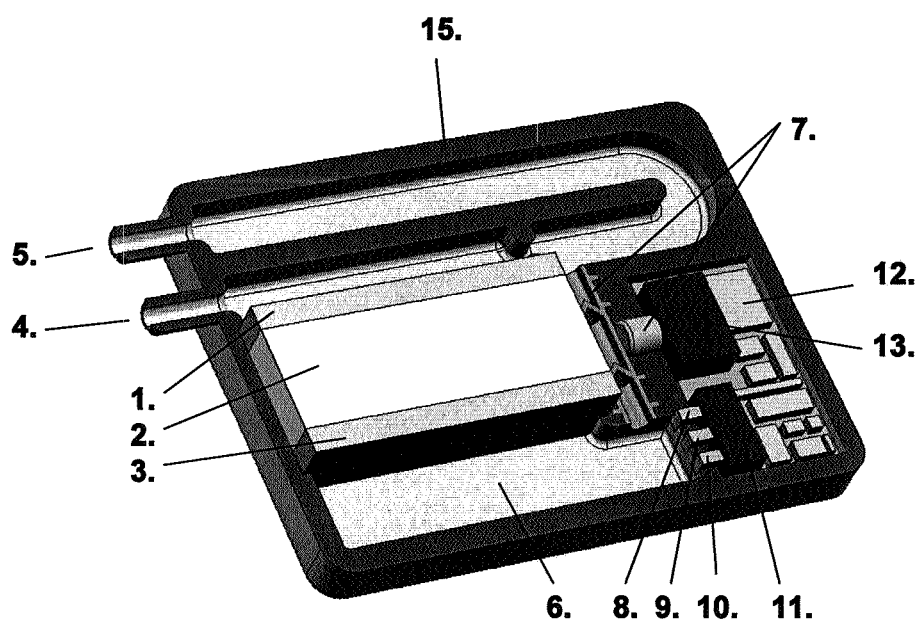
FIG. 2 shows an opened out 3D-model of a device described in FIG. 1.
Figure 3:
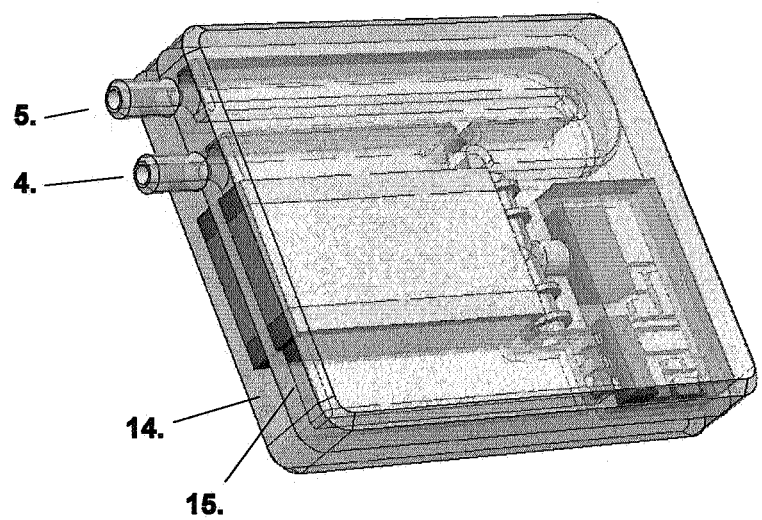
FIG. 3 is an artist's impression of an assembled device as described in FIGS. 1 and 2.
Figure 4:
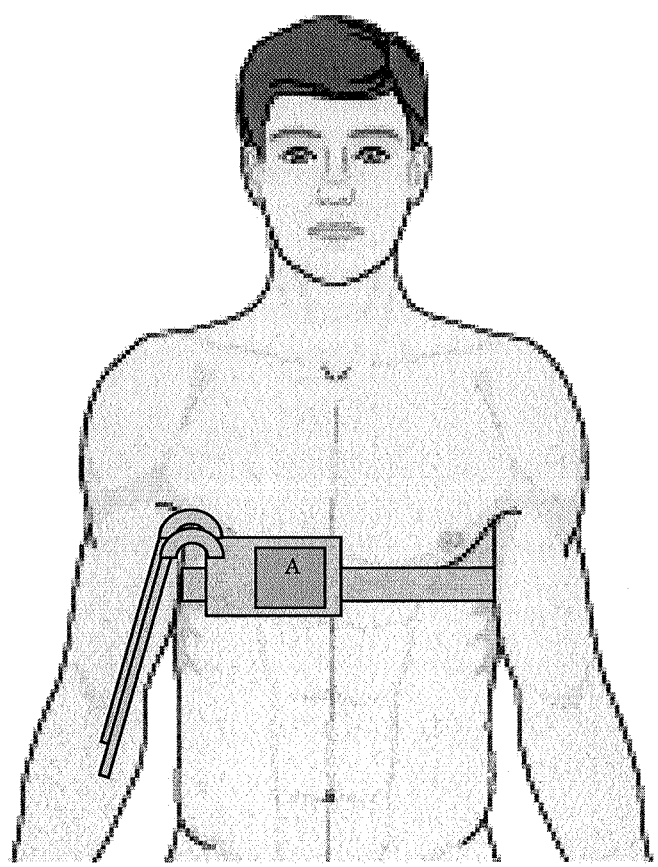
FIG. 4 shows an example of a wearable artificial kidney system comprising the filter pad of the invention (indicated by the letter A) fitted to a belt and provided with conduits for blood feed and blood return.
Figure 5:
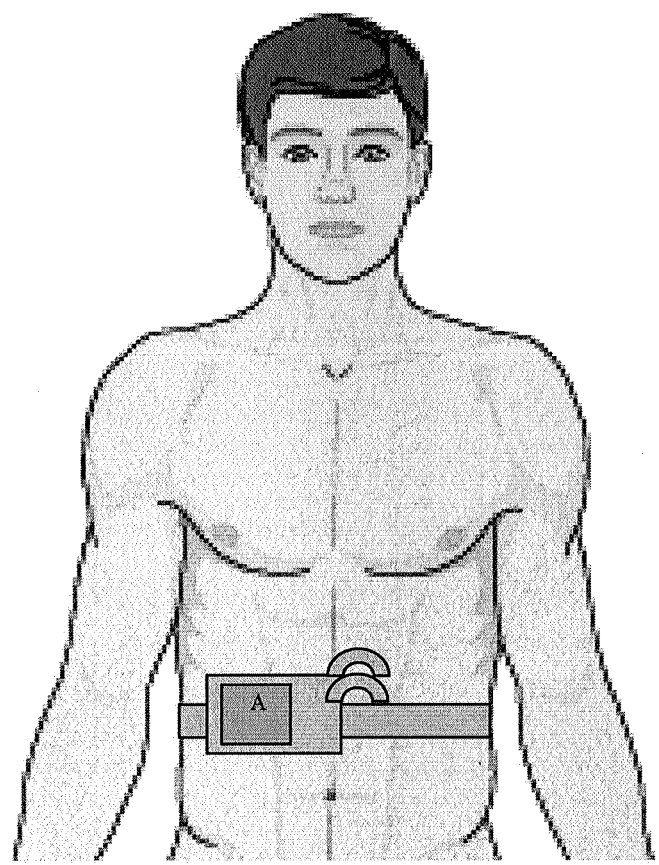
FIG. 5 shows an example of a wearable peritoneal dialysis system comprising the filter pad of the invention (indicated by the letter A) fitted to a belt and provided with conduits for feed and return of peritoneal dialysis fluid.
Figure 6:
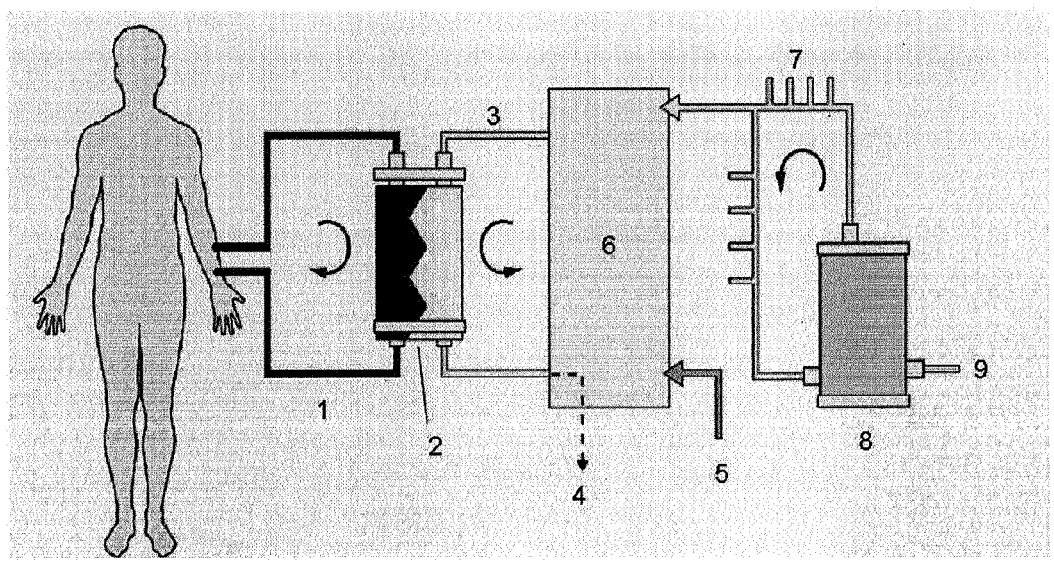
FIG. 6 shows the prior art hemodialysis procedure indicating the extracorporeal circuit (1); the dialyzer (2); the dialysis fluid circuit (3); waste outlet (4); concentrated dialysate input (5); dialysis machine (6); treated water (7); water purification (8); and source water (9). The system uses in general 120 liters of dialysate per treatment, employs a low osmotic pressure difference, uses a low to medium flux hemofilter and removes only small molecules. All these items may be replaced by a hemofiltration unit as shown in FIG. 7 below.
Figure 7:
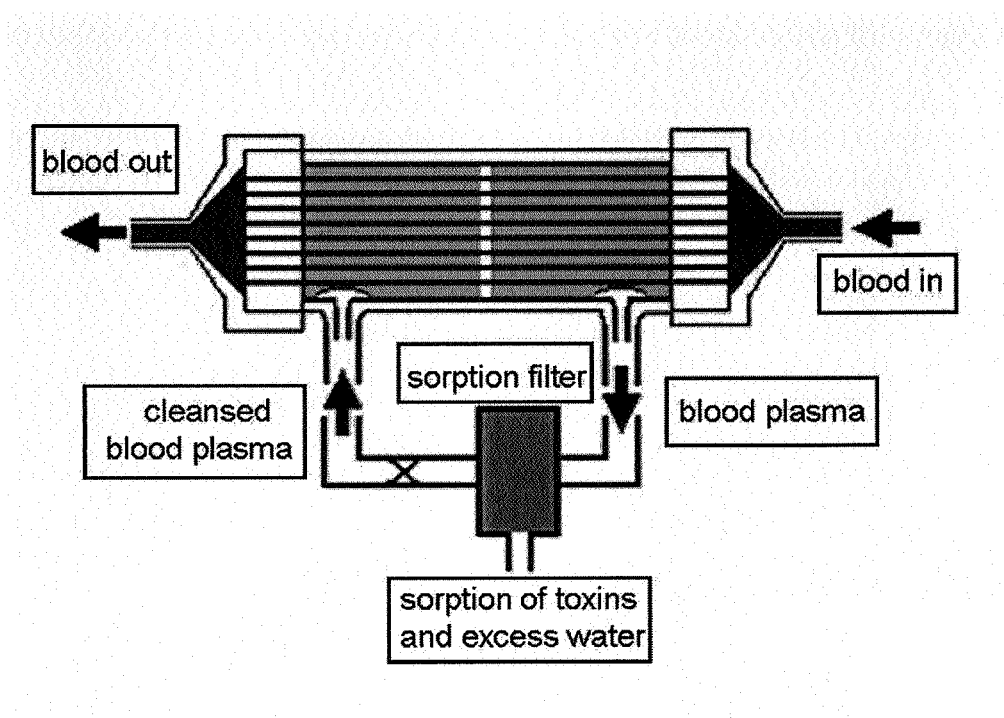
FIG. 7 shows a hemofiltration unit of the present invention comprising a blood inlet and outlet, a hemofilter for separating blood cells from plasma, and a blood plasma circuit running across a sorption filter according to the present invention for the sorption of toxins and excess water. The hemofilter is provided with a barrier (blank bar in the middle) to separate the blood inlet part from the blood outlet part, in order to force the plasma through the sorption filter. Such a system features direct filtration of blood plasma and extraction of compounds from the plasma, consumes no dialysate and requires no water treatment equipment and uses high flux hemofilter through which albumin can pass. The a sorption pad filter system removes not only the "standard" toxins from the blood such as small molecules like potassium, phosphate, and urea, but also toxic substances which are not removed by prior art hemodialysis systems. In particular, the sorption pad of the invention also clears middle molecules such as creatinine, beta2-microglobulin ($\beta$2M), protein-(albumin) bound toxins such as bilirubin. This results in a much better health condition of ESRD patients.
Figure 8:
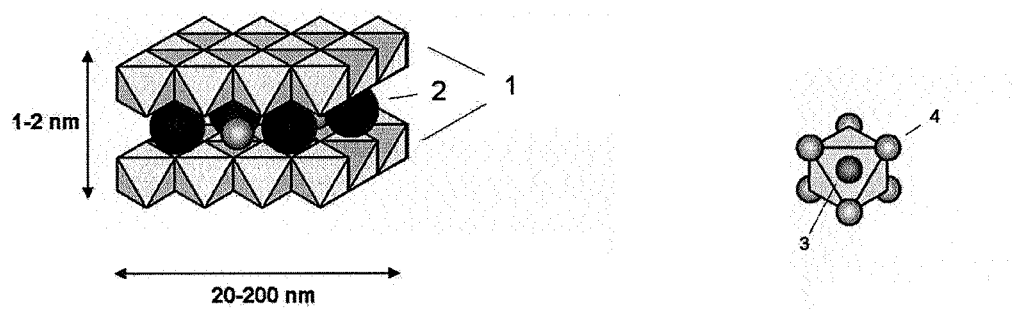
FIG. 8 shows the layered crystal structure of hydrotalcite-like compounds (layered double hydroxides; LDHs): numbers indicate hydroxide layers ($[M^{II}_{1-x}M^{III}_{x}(OH)_{2}]^{x+}$) (1) and interlayer containing An—anions (large spheres) and water molecules (small spheres) (2); individual hexahedral structure of the metal hydroxide is shown on the right indicating the metal (II or III) atom (3) and hydroxide groups (4).
Figure 9:
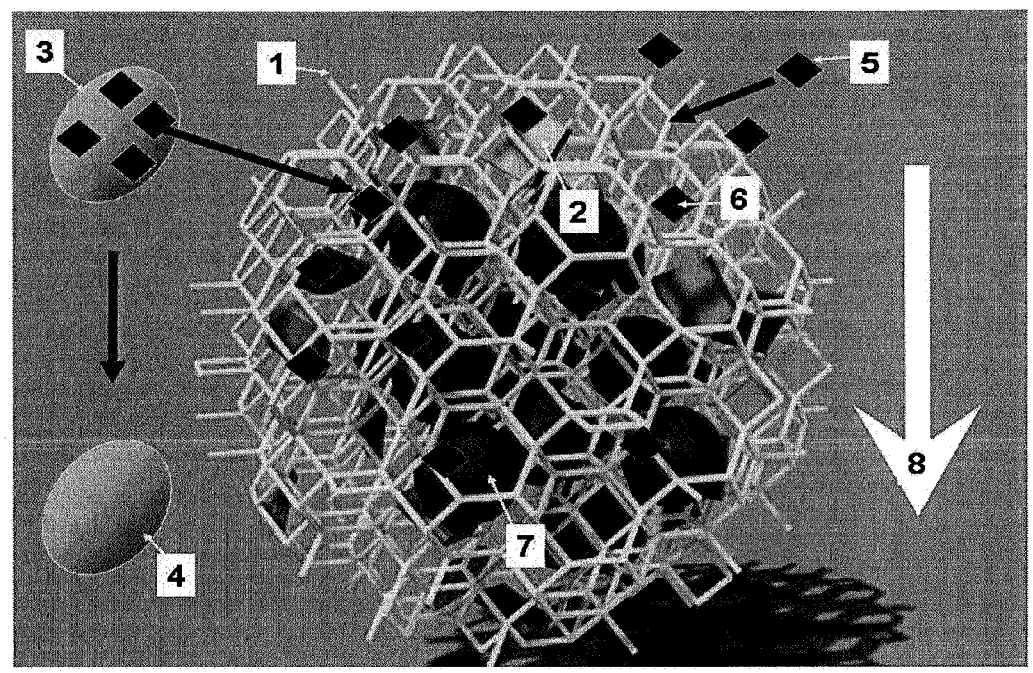
FIG. 9 shows a sorption bead or sorption granule according to the present invention comprising a nanoporous (biopolymer) matrix functionalised with nanoparticles (nanoclays or hydrotalcites, in particular precipitated metal hydroxides) creating a high, selective sorption power. Numbers indicate the following (1): nanoporous biopolymer, in particular a modified starch with tuneable porosity for selective uptake of small and middle molecules; (2): sorption nanoclay or hydrotalcite, preferably functionalized for sorption of anions, cations and (toxic) proteins; (3): albumin with bound toxins; (4): cleared albumin; (5): free toxins; (6) and (7): trapped toxins, sorbed molecules, ionic solutes and small molecules at the inside, middle molecules at the outside of the bead; (8): blood flow.

A device of the present invention can take the form of a wearable or desktop sized artificial kidney based on combined ultrafitration and sorption-filtering. In such an embodiment, the ultrafiltration step will performed by a special high flux hemofilter, with a relative large poresize, that separates blood from bloodplasma, allowing toxic solutes, small/middle molecules and albumin with bound toxins to pass with the bloodplasma into the compartment with the sorption filter pad for cleansing. Via an additional hemofilter with a smaller poresize, excess water can be removed from the blood plasma preventing loss of albumin. The cleansed bloodplasma is then re-entered into the bloodstream. It will be understood that in such an embodiment, the device further comprises the necessary tubing, vascular access and feedback systems, pumping, electronics, sensors, power packs and other requirements. However, these are not essential to the present invention. An advantage of the artificial kidney device is that no dialysis fluid will be needed. In a preferred embodiment of this device, the hemofilter and sorption-filter are being combined to form a filter pad, said filter pad comprising an envelop surrounding a filter pad contents, wherein the envelop of said pad comprises said hemofilter, and the contents of said pad comprise said sorbent material. The hemofilter may consist of a material that completely surrounds the sorbent material, or it may form a "window" in the envelope surrounding the sorbent material on the side where the blood is supplied to the filter pad. In other embodiments of a device of the invention the hemofilter comprises an inlet for receiving blood from a patient, and at least one outlet for recovery of patient blood plasma. In addition, the hemofilter may comprise at least a further outlet for recovery of patient blood cells. A representative embodiment of a device of the present invention is depicted in FIGS. 1, 2 and 3. The device as depicted in FIG. 1 is a cross-sectional presentation of a device, for which an opened-out 3-D model is drawn in FIG. 2. FIG. 3 provides an artist impression of an assembled device of FIG. 2 showing the various components of FIGS. 1 and 2 in transparent housing. Numbering is the same for all parts in the three figures. The device as depicted in FIG. 1 further comprises a blood (or general fluid) inlet (4), which may be connected to vascular access and tubing; a blood (or general purified fluid) outlet (5), which is provided for recovery of blood cells and filtered blood plasma; a blood plasma outlet (6) for the recovery of filtered blood plasma flowing out of the sorption filter and bottom hemofilter; a (micro)-pump (7); at least one sensor (8), (9), and/or (10) for measuring salt and/or small and/or middle-sized molecule content, etc.; electronic components (11) (e.g. for digital signal processing (DSP), interfaces for sensors); a RF-wireless radio module (12) providing a link to a medical consultant or computer; a power supply for the device (e.g. incl. power supply for the pump) and accompanying electronics and mechatronic part for the pump (13); a housing, optionally comprised of a monolithic structure, but preferably comprising a first part (14, not drawn) and a second

(15) part, which first and second part are separably connected to each other possibly combined with integrated or separate liquid and airtight sealing gaskets to provide the enclosure for the various components of the device, and which, when separated, provide access to the interior of the device. The housing (parts) (14, 15) are suitably injection moulded or otherwise formed plastic housing parts. The sensor(s) (8), (9), and/or (10), and optionally more, may also be located at other positions and can be provided in configurations capable of measuring such parameters as biofilm formation, clothing of blood and microbial contamination. The letters A-F indicate: blood patient (A); blood return (B); cleansed blood plasma (C); excess water outlet (D); sorption filter pad (E); and blood plasma flow across sorption filter pad (F). The outlet system to dispose off of excess water (D) may take the shape of a simple drain (valve under the filter package) connected to a tube, container, a fluid absorbing package etc. It will be understood that the device of the present invention may take various shapes and the various components may take various positions relative to each other. In fact, the skilled person is free in the design of the device and the location of the various components as long as functionality will be maintained.

The hemofilter in a device of the present invention is preferably a commercially available hemofilter (e.g. such as produced by Gambro GmbH, Hechingen, Germany or Membrana GmbH, Wuppertal, Germany).

In an alternative embodiment the sorption-filter in a device of the invention may comprise an inlet for receiving patient blood plasma exiting said hemofilter, and at least one outlet for recovery of purified blood plasma.

A device of the present invention may, in any embodiment, further comprise means for supplementing the (purified) blood plasma or dialysate fluid with at least one substance selected from the group consisting of vitamins such as vitamins A,C and B12; minerals such as calcium, sodium and potassium; anticoagulants; anti microbial agents and other medicaments.

A device of the present invention may, in any embodiment, further comprise means for selective sorption of middle molecules, vitamins and minerals such as calcium, sodium and potassium. The sorption materials as described (smectites, nanoclay, layered double hydroxides, hydrotalcites, crystallisation seeds, metal organic frameworks, modified biopolymers etc.) are therefore loaded with a certain amount of minerals, vitamins and can only absorb a designated amount.

A device of the present invention may, in any embodiment, further comprise means for selective sorption of middle molecules, vitamins and minerals such as calcium, sodium and potassium in the sorption pad via osmotic differences between blood and dialysate fluid in combination with the filterpad. The blood plasma in this variant essentially remains in circulation and does not enter as a whole the filter pad, but is being cleaned from toxic substances and is being supplemented with nutrients and other vital substances via the dialysate fluid in combination with the sorption unit.

Optionally, the device or filter pad may comprise ion exchange systems.

In another aspect, the present invention provides a method for removing toxic substances from blood, comprising using a device according to the present invention.

In another aspect, the present invention provides a method for removing toxic substances from hemodialysis or peritoneal dialysis fluids, comprising using a device according to the present invention.

The sorption filter in a device of the present invention may take the form of a filter pad, consisting of a rigid or flexible container comprising the sorbent materials.

Thus, in another aspect, the present invention provides a filter pad for separating blood into plasma and cells and for purifying the plasma thus obtained, said filter pad comprising an envelop surrounding a filter pad contents, wherein the envelop of said pad comprises a hemofilter, and the contents of said pad comprise sorbent material for extracting small and middle-sized molecules from said plasma.

The Nanostructured Sorption Material Comprised in the Sorption Filter

The nanostructured material exhibits sorption capacity of various substances, based on ion-exchange, surface nucleation (surface crystallisation) activity and/or surface adsorption activity.

The sorption material is preferably functionalized, such as to exhibit improved sorbing properties of toxic substances such as urea as compared to the non-functionalized material. The sorption material in the present invention is a nanomaterial, meaning that the material consists of particles or contains particles with a size of preferably 100 nanometres or less in order create a large specific surface area. The nanomaterials will enable very high sorption efficiency and therefore enable a small sized, lightweight and ultimately wearable dialysis machine.

Typically the nanostructured sorption material will exhibits ion exchange or intergallery or intergalleries filtering. Intergalleries are the spaces between the single crystals of minerals which make up the nanostructured material. Preferably, ion exchange relates to anion exchange and/or cation exchange, with anions such as $Cl^-$, $Br^-$, $I^-$, $SO_4^{2-}$, $PO_3^{3-}$, $NO_3^-$, $CO_3^{2-}$, $RCOO^-$ (carboxyl group, wherein R is a organic substituent) etc., and cations such as $K^+$, $Ca^{2+}$, Na, $Cu^{2+}$, $Zn^{2+}$, $Al^{3+}$, $NH_3^+$, $R_xNH_y^+$ (an aliphatic amine, wherein R is a organic substituent, x is en integer from 1 to 3, and y is an integer from 0 to 2), etc.

In general, suitable nanostructured sorption materials with ion-exchange and/or surface nucleation activity are layered double hydroxides (anionic clays). Layered double hydroxides (LDH's) are a class of ionic lamellar solids with positively charged layers with two kinds of metallic cations and exchangeable hydrated gallery anions. Layered double hydroxides (LDHs) comprise an unusual class of layered materials with positively charged layers and charge balancing anions located in the interlayer region. Phyllosilicates usually have negatively charged layers and cations in the interlayer spaces. LDHs are therefore also referred to as anionic clays or as hydrotalcite-like compounds. Hydrotalcite-like compounds (HT) can be represented by the following formula: $[Mg_{1-x}Al_x(OH)_2]^{x+}[A_{x/n}{}^{n-}.mH_2O]^{x-}$, wherein $0 \leq x \leq 0.33$, and $A^{n-}$ is an exchangeable anion having a valence of n. These compounds are similar to the mineral hydrotalcite, $Mg_6Al_2(OH)_{16}CO_3 \cdot 4H_2O$. LDH's may have different cations, such as Mg, Mn, Fe, Co, Ni, Cu and/or Zn as divalent cations, and Al, Mn, Fe, Co, Ni, Cr and/or Ga as trivalent cations. Processes for the production of synthetic LDHs are inter alia described in U.S. Pat. No. 3,539,306 and U.S. Pat. No. 3,650,704.

A layered double hydroxide material (LDH) for use in aspects of the present invention is composed of small crystalline sheets of sub-micron dimensions, between which anions are located. U.S. Pat. No. 4,904,457, which is incorporated herein by express reference thereto, describes possible methods of preparation for a synthetic layered double hydroxide. Preferably, the layered double hydroxide has a large contact surface and an ion exchange capacity of 20 to 600 milliequivalents per 100 grams. An LDH preferably used is a hydrotalcite or a hydrotalcite-like material, because these materials can be readily prepared synthetically and the desired properties can be closely controlled during synthesis as will be readily determined by those of ordinary skill in the art.

In general, particularly suitable nanostructured sorption material with ion-exchange and/or surface nucleation activity is a hydrotalcite comprised of a mixture of magnesium and aluminium hydroxide in the form of a layered, anion intercalation compound. It is generally utilized as acid adsorbent, catalyst carrier, and anion exchanger. Particularly preferred hydrotalcites are $Mg_2Fe(OH)_6.OH$ and $Mg.OH$. It should be noted that hydrotalcites used in aspects of the present invention need not be layered, but may be provided in the form of nanocrystalline materials.

In general, suitable nanostructured sorption materials are small nano-sized particles, that induce surface crystallisation by mimicking the morphology of the chemical species to be removed such as urea crystals or urea coated particles. These heterogeneous seeds are generally used in filter assisted crystallisation processes. The sorbing process is based on induction of crystallisation of the species to be removed and subsequent filtering of the crystallites.

"Nano sized" as used herein, refers to a size of approximately 1-1000 nm, more preferably 1-100 nm.

A suitable sorption material with ion-exchange and/or surface nucleating activity is a clay, in particular a nanoclay. The clay material may be of a natural or synthetic nature. Preferably, the clay has a large contact surface. Very suitable are clay types based on layered silicates, such as layered phyllosilicate composed of magnesium and/or aluminum silicate layers which are each about 7-12 Å in thickness. Especially preferred are smectite-like clay minerals, such as montmorillonite, saponite, hectorite, fluorohectorite, beidellite, nontronite, vermiculite, halloysite and stevensite. Preferred are smectite, hectorite, saponite, and montmorillonite.

The term "nanoclay" refers to a clay (hydrous aluminium phyllosilicate), preferably from the smectite family, having a unique morphology, featuring one or more dimensions, such as length, width, or thickness, in the nanometer size ($10^{-9}$ meter). The nanoclay may be described as consisting of extremely fine platelets, each having a high aspect ratio and large surface area. Montmorillonite clay is the most preferred smectite clay. The smectite clay particle, or platelet, is a sheet-like structure separated by interlayers. The interlayers may be intercalated with an intercalant, the intercalate representing a clay-chemical complex wherein the clay gallery (interlayer) spacing has increased, due to swelling resulting from surface modification by an intercalant, which often involves cation exchange processes. Under the proper conditions of temperature and shear, an intercalate is capable of exfoliating in a resin matrix, wherein the lamellar-structure of the clay is degraded, and the clay ultimately exfoliates into individual sheets. An intercalant is an organic or semi-organic chemical capable of entering the clay gallery and bonding to the surface. Exfoliation describes a dispersion of a surface treated nanoclay in a plastic matrix. In exfoliated form, nanoclay platelets have a flexible sheet-type structure, which is remarkable for its very small size, especially the thickness of the sheet is astoundingly small, measuring only about a nanometer. The length and breadth of the particles range from 1.5 μm down to a few tenths of a micrometer. These dimensions result in extremely high average aspect ratios (75-500). Moreover, the miniscule size and thickness mean that a single gram contains over a million individual particles. The nanoclays may be used in the form of nanocomposites, i.e. a combination of a surface treated nanoclay and a resin matrix.

Clays are commonly provided as particles having compositions based on hydrated aluminum silicates. The dimensions of the clay particles are typically in the range from 100 nanometers (nm) to 10 microns. Certain clay particles have structures containing multiple layers or stacks of clay platelets. Under suitable conditions, the stacks of clay platelets can be partially or completely separated to individual clay platelets. As used herein, the term "exfoliated clay" refers to a clay in the form of separated clay platelets having only one dimension in the range of nanometers and the other two dimensions in a larger size range, such as 100 nanometers and greater. As used herein, the term "to exfoliate" refers to the process of separating individual platelets from a clay particle or a stack of clay platelets, wherein the clay platelets have only one dimension in the range of nanometers and the other two dimensions in a large size range, such as 100 nanometers and greater. Typical size ranges for the exfoliated clays are platelets having one dimension, referred to as the thickness, in the range of from 1 nm to 20 nm, preferably in the range of from 1.5 nm to 15 nm, and more preferably in the range of from 2 nm to 12 nm. The other two dimensions of the platelet, which form the two faces of the platelet, are larger than the platelet thickness, and are typically in the range of from 50 nm to 20 microns, preferably in the range of from 75 nm to 15 microns, and more preferably in the range of from 100 nm to 10 microns. Surface areas for a platelet face are typically in the range of 2500 square nanometers to 400 square microns.

A clay suitable for use as nanostructured sorption material in aspects of the present invention typically has a layered structure. A suitable clay type has a cation exchange capacity of between 30 and 250 milliequivalents per 100 gram. If a clay with a cation exchange capacity higher than 250 milliequivalents per 100 gram is used, it will be difficult to finely disperse the clay at a molecular level due to the strong mutual interaction between the clay layers. If a clay with a cation exchange capacity lower than 30 milliequivalents per 100 gram is used, it will be difficult to modify the clay due to the fact that the interaction with the polymer will be weak. Preferably a clay having a cation exchange capacity of between 50 and 200 milliequivalents per 100 gram is used. Very suitable are clays based on layered silicates, such as layered phyllosilicates composed of magnesium and/or alumina silcate layers, each having a thickness of 7-12 Å. The clay may have a natural or synthetic origin. Preferably the clay has a large contact surface. Very suitable clays are clays from the synthetic small smectites and/or smectite-like clays such as montmorillonite, hectorite, fluorohectorite, beidellite, nontronite, bentonite, saponite, vermiculite, halloysite and/or stevensite.

The nanoclay is preferably an exfoliated nanoclay.

The nanoclay used in aspects of the invention may be a nanocomposite. There are in principle three possible structures when nanoclays are added to polymers: i) phase separated, wherein the nanofillers are intact and phase separated from the polymer, intercalated, wherein the polymer has entered the clay gallery; and iii) exfoliated, wherein the clay platelets are dispersed in the polymer. The latter two are forms of nanocomposites. Nanocomposites are compositions containing a dispersed material that has one or more dimensions, such as length, width, or thickness, in the nanometer size range. Thus, polymer-clay nanocomposites typically are characterized as being one of several general types: an intercalated nanocomposite, an exfoliated nanocomposite, or combinations thereof. The term "intercalated nanoclay" as used herein, describes a nanoclay that is characterized by the regular insertion of a polymer in between the clay layers, wherein the individual clay platelets are not completely separated from the clay particle. The term "exfoliated nanoclay", as used herein, describes a nanocomposite wherein the clay is dispersed in a polymer matrix mostly as individual platelets having a single dimension, the thickness, in the nanometer size range. The exfoliated nanocomposite maximizes the polymer-clay interactions as the entire surface of the clay platelet is in contact with the polymer matrix. This modification often leads to the most dramatic changes in the mechanical and physical properties of the resultant polymer. In contrast, a conventional (phase separated) composite is a composite in which the clay acts as a conventional filler and is not dispersed on a nanometer size scale. In certain embodiments of the present invention, some portion of the clay in the polymer-clay nanocomposite optionally exists as structures larger than exfoliated or intercalated composites.

The (polymer) nanocomposites used in aspects of the present invention may suitably be based on clays, layered silicates and layered double hydroxides (hydrotalcites). The nanocomposites are typically obtained by the intercalation or penetration of the polymer (or a monomer subsequently polymerized) inside galleries of layered clay material and optionally the subsequent exfoliation, or dispersion, of the intercalate throughout the polymer matrix.

The term "nanostructured material" (also interchangeably referred to herein as "nanomaterial" or "nanostructured sorption material") is defined herein as a material having at least one dimension in the nanometer-size. A nanometer (nm) is $10^{-9}$ meter, therefore, nanometer-size range encompasses from about 1 to 999 nm. The nanostructured materials may be natural, modified, or synthetic in nature, or any combination thereof. Nanostructured materials particularly suitable for use in aspects of the invention include one or more of the following categories of nano-sized materials: nanoparticles or nanocrystalline materials, nanoporous materials, nanocomposites, nanoclays and nanofibers (nanotubes and nanowires), and any combination thereof. A nanostructured material might, for example, contain a single nanocrystalline material or it might contain two nanocomposites combined with a type of nanoparticle.

Nanocrystalline materials (the terms nanoparticles, nanocrystalline materials and nanopowders are used interchangeably herein) are nano-sized crystallites, preferably about 1 to 10 nm in dimension, and having an ultrahigh surface-to-volume ratio. The nanocrystalline materials may be synthesized de novo by precipitation or may be prepared by the size reduction of larger particles.

The use of nanocrystalline materials, for instance based on metal oxides and metal hydroxides for deodorizing an enclosed space is e.g. known from WO 2007/051145. Preferred nanocrystalline materials for use in connection with the present invention include the metal oxides and metal hydroxides of Mg, Sr, Ba, Ca, Ti, Zr, Fe, V, Cr, Co, Y, Mn, Ni, Cu, Al, Si, Zn, Ag, Au, Mo, Sb, Ce and mixtures thereof. The nanocrystalline materials may be optionally coated as disclosed in U.S. Pat. Nos. 6,093,236, and 5,759,939, may be halogenated as disclosed in U.S. Pat. Nos. 6,653,519, 6,087,294 and 6,057,488 or in other ways modified as described in e.g. U.S. Pat. No. 6,887,302 and US, all of which are incorporated by reference herein. The nanocrystalline materials preferably present crystallite sizes of less than about 25 nm, more preferably less than 20 nm, and most preferably less than 10 nm. The nanocrystalline particles preferably exhibit a Brunauer-Emmett-Teller (BET) multipoint surface area of at least about 100 m$^2$/g, more preferably at least about 300 m$^2$/g, and most preferably from about 700 m$^2$/g and more. Exemplary nanocrystalline materials are available from NanoScale Materials, Inc., Manhattan, Kans., under the name NanoActive®.

Nanopowder materials, which term refers in particular to nano-structured metal powders, preferably nanopowders of metal oxides or nano-metal hydroxides, may for instance be produced by the reduction of metal salts, oxides or hydroxides to a powder consisting of ultrafine metallic or non-metallic particles in the nano-scale range (5-100 nm). Nanopowders of metal oxides or hydroxides can for instance be produced by subjecting a solution of a salt of the metal (generally a chloride) in a suitable solvent (e.g. water) to ultrasound waves (up to 0.6 W/cm3) in the presence of a base, such as e.g. an alkali hydroxide. Under such conditions, highly active radicals are rapidly created inside cavitation bubbles, that explode rapidly, leaving nuclei of nano-particles (for more details see e.g. WO 2003/012800). Examples of nanoparticle compounds which can be produced in this way include nanoparticles of metals, metal oxides and metal hydroxides. In principle, any metal may be used including but not limited to Mg, Sr, Ba, Ca, Ti, Zr, Fe, V, Cr, Co, Y, Mn, Ni, Cu, Al, Si, Zn, Ag, Au, Mo, Sb, Ce etc. and combinations thereof. Also non-metals can be included in the nanopowder material, and for instance hydroxyapatite (pentacalcium hydroxide triphosphate) may be produced in nanopowdered form. Alternatively nanopowder materials may be produced as inorganic nanoparticles using flame-spray synthesis technology (e.g. US 2006/162497).

Nanoporous materials are characterized by the molecular assembly of structures consisting of nanometer-sized cavities or pores. Nanoporous materials for use in the present invention may include nanoporous silica's, nanoporous alumina silicates (such as zeolites). The nanoporous materials may be based on natural materials or may be synthetically prepared.

Very suitable nanoporous materials for use in the present invention are metal organic frameworks (MOFs). Metal organic frameworks are hybrid materials where metal ions or small nano-clusters are linked into one-, two- or three-dimensional structures by multi-functional organic linkers as described, for example, in U.S. Pat. Nos. 5,648,508 and 6,893,564. Among the advantages of these materials are: (i) larger pore sizes can be realized than for the zeolites used presently (ii) the internal surface area is larger than for porous materials used presently (iii) pore size and/or channel structure can be tailored over a large range, (iv) the organic framework components forming the internal surface can be functionalized easily. In many cases it is possible to obtain open micro- and mesoporous structures having high porosities and specific surface areas of even above 5000 m2/g. Such open, porous, structures are very suitable for use as nanostructured adsorbents in the present invention. In addition it is possible to use conventional organic procedures to introduce a variety of functional groups in the organic part of the framework, thereby tailoring the affinity towards reactants and host molecules. The metal organic frameworks for use in the present invention may be based on Mg, Sr, Ba, Ca, Ti, Zr, Fe, V, Cr, Co, Y, Mn, Ni, Cu, Al, Si, Zn, Ag, Au, Mo, Sb, Ce or any other metal that provides good adsorption characteristics. The preferred metals in applications for dialysate fluid or blood (plasma) purification in nanostructured materials used in aspects of the present invention are preferably based on metals such as Fe, Ti and Mg. Other metals could be harmful to the body when inadvertently released form the matrix.

Typical nanostructured materials of the present invention may be based on aluminosilicates. Aluminosilicate nanostructured materials include, but are not limited to, layered polysilicates such as magadiite and kenyaite, polysilicates such as wollastonite, phyllosilicates such as the smectite group of clay minerals, tectosilicates such as zeolites, tetrasilicates such as kenyaite, and zeolites. Natural or synthetic phyllosilicates, for example, are sheet structures basically composed of silica tetrahedral layers and alumina octahedral layers. Phyllosilicates are one of the preferred types of nanostructured material, and a preferred type of phyllosilicate includes one or more smectite clays alone or in combination with other compatible structured nanomaterials. Additional examples of phyllosilicates useful in the present invention include, but are not limited to, montmorillonite, nontronite, beidellite, hectorite, saponite, sauconite, kaolinite, serpentine, illite, glauconite, sepiolite, vermiculite, or mixtures thereof. Though not restricted in particular, the total cation exchange capacity of the phyllosilicates can preferably be 10 to 300 milliequivalents, more preferably from 50 to 200 milliequivalents, per 100 grams of the phyllosilicate material. Phyllosilicate nanomaterials (i.e., nanoclays) are commercially available from Nanocor, Inc. of Arlington Heights, Ill. as NANOMER and from Southern Clay Products, Inc. of Gonzales, Tex. as CLOSITE.

Tectosilicates and tetrasilicates are another class of synthetic or natural aluminosilicates that are crystalline porous nanostructures having long-range crystalline order with pore sizes that may be varied from about 2 Å to 200 Å(Angstroms). The zeolite aluminosilicates may be divided into those with a fibrous habit and an underlying chain structure (i.e., natrolite); those with a platy habit and an underlying sheet structure (i.e., heulandite); and those with an equant habit and an underlying framework structure (i.e., chabazite). Zeolites may be synthesized by any technique known to those who are skilled in the art, such as that taught in U.S. Pat. No. 5,098,684, which is incorporated herein by express reference thereto.

The nanostructured material may be a carbonaceous nanomaterial. Carbonaceous nanomaterials suitable for use in aspects of the present invention include fullerenes, carbon nanoparticles, diamondoids, porous carbons, graphites, microporous hollow carbon fibers, single-walled nanotubes and multi-walled nanotubes. Fullerenes typically consist of 60 carbon atoms joined together to form a cage-like structure with 20 hexagonal and 12 pentagonal faces symmetrically arrayed. Preferred fullerene materials include $C_{69}$ and $C_{70}$, although other "higher fullerenes" such as $C_{76}$, $C_{78}$, $C_{84}$, $C_{92}$, and so forth, or a mixture of these materials, could conceivably be employed. Graphite is a crystalline form of carbon comprising atoms covalently or metallically bonded in flat layered planes with weaker van der Waals bonds between the planes.

Diamondoids are three-dimensional polycyclic organic compounds that may be substituted or unsubstituted. The term "lower diamondoids" refers to all isomers and stereoisomers of adamantane, diamantane, triamantane, or mixtures thereof. The term "higher diamondoids" refers to all isomers and stereoisomers of tetramantane, pentamantane, hexamantane, heptamantane, octamantane, nonamantane, decamantane, undecamantane, or mixtures thereof. The lower diamondoids may be synthesized or refined from a natural gas stream in a two stage separation process, e.g., as described in U.S. Pat. No. 4,952,748, the disclosure of which is incorporated herein by express reference thereto. The higher diamondoids may be isolated or purified from natural gas condensates or refinery streams through pyrolysis, distillation, pyrolysis/distillation, preparative gas chromatography, high performance liquid chromatography, crystallization, recrystallization, thermal diffusion, or fractional sublimation, as described in WO 02/058139.

Carbon nanotubes may be a single layer or multiple layers of the hexagonal lattice graphite, wrapped into a cylindrical tube, typically of about 1 nanometer diameter, but up to several microns long. This gives an aspect (or length-to-diameter) ratio that can be in excess of 10,000. The nanotubes may be further grown into partially ordered two-dimensional bundles, or "ropes" formed from individual nanotubes. Carbon nanotubes are typically prepared from the decomposition of carbon-containing gases over selected catalytic metal surfaces at temperatures ranging from about 500° C. to about 1,200° C., such as that described in U.S. Pat. No. 6,517,800, the disclosure of which is incorporated herein by express reference thereto.

The nanostructured materials of the present invention can include refined but unmodified nanomaterials, modified nanomaterials, synthetic nanomaterials, or mixtures thereof. The nanomaterials of the present invention may be dispersed directly into the polymer matrix, or may be dispersed with further intercalation or exfoliation processing, or some combination thereof. The intercalation or exfoliation processes may be conducted before, during, or after mixing the nanomaterials with the polymer matrix. However, it is not intended that these methods be limited to any specific process or procedure, and any suitable intercalation or exfoliation or combination thereof available to those of ordinary skill in the art may be used in accordance with the invention described herein.

"Intercalation" is defined as the insertion of mobile guest species (atoms, molecules, or ions) into a crystalline host lattice that contains an interconnected system of empty lattice sites of appropriate size. Intercalation is typically reversible, meaning that the structural integrity of the host lattice is formally conserved in the course of forward and reverse reactions.

An intercalated nanostructured material may be prepared, e.g., by the reaction of one or more swellable nanomaterials with a swelling agent of one or more organic molecules or cations. The process to prepare the intercalated nanomaterials may be conducted in a batch, semi-batch, or continuous manner. Numerous methods to modify nanomaterials with organic cations, such as those taught in U.S. Pat. No. 4,810,734, which is incorporated herein by express reference thereto, are known, and any of these may be used in the practice of this invention.

Organic molecules suitable as swelling agents include cationic surfactants such as ammonium, phosphonium or sulfonium salts; amphoteric surface active agents; derivatives of aliphatic, aromatic or arylaliphatic amines, phosphines and sulfides; and organosilane compounds. Other suitable swelling agents include protonated amino acids and salts thereof containing 2-30 carbon atoms such as 12-aminododecanoic acid, epsilon-caprolactam and like materials. A preferred swelling agent includes ammonium to effect partial or complete cation exchange. The intercalation process results in the development of intercalates which are more organophilic and which can be more readily exfoliated (dispersed) during admixture with a polymer to form an ionomeric nanocomposite. These intercalates are typically on the order of 1 nanometer thick, but about 100 to 1,000 nanometers across. This high aspect ratio, and the resulting high surface area, provides high reinforcement efficiency at low loading levels.

Intercalation may also be accomplished by dispersing the nanostructured materials in a solution containing an oxidizing agent, e.g., a mixture of nitric and sulfuric acid, as described in U.S. Pat. No. 3,404,061, the disclosure of which is incorporated herein by express reference thereto. The intercalation solution contains oxidizing and other intercalating agents known in the art. Examples include those containing oxidizing agents and oxidizing mixtures, such as solutions containing one or more of nitric acid, potassium chlorate, chromic acid, potassium permanganate, potassium chromate, potassium dichromate, perchloric acid, and the like, or mixtures of a strong organic acid, e.g., trifluoroacetic acid, and a strong oxidizing agent soluble in the organic acid. The intercalation solutions may further include electron donors (e.g., alkali metals, alkaline-earth metals, lanthanides, metal compounds containing hydrogen or polar molecules, and aromatic compounds) or electron acceptors (halogens, halides, oxyhalides, and acids) in an organic solvent. After intercalation, excess solution is removed, typically by driving off the solution by heat treating the mixture. In addition, the intercalation process may use an electrolytic intercalation solution in which the nanostructured material is subjected to electrolysis, dried, and then heated to temperatures up to 1,000° C.

A sorbent material of the present invention, comprising a nanostructured sorption material captured in a porous polymer matrix, may be prepared by providing the nanostructured sorption material and the porous polymer matrix separately and combining the two such that the nanostructured sorption material is inserted in the porous polymer matrix. This may for instance occur by instilling the polymer matrix with a suspension of the nanostructured material.

Alternatively, in order to obtain a polymer matrix having a nanostructured material dispersed therein, one may prepare the matrix having the desired porosity, and synthesize the nonostructured material therein. Very suitable the polymer matrix may be imbibed with a solution of a metal salt which may then be precipitated the metal salt in the form of a metal hydroxide or metal oxide in the matrix.

The Polymer Matrix

The invention relates to a sorbent material comprising a polymer for retaining the nanostructured sorption material. In other to provide for a matrix having a specific pore size, the polymer in preferred embodiments is a cross-linked polymer. In other preferred embodiments the polymer is a charged polymer. Polymers used in aspects of the invention may be synthetic or natural polymers.

Natural polymers (biopolymers) suitably comprise a cross-linked carbohydrate or protein, made of oligomeric and polymeric carbohydrates or proteins. The biopolymer is preferably a polysaccharide. Examples of polysaccharides include α-glucans having 1,3-, 1,4- and/or 1,6-linkages. Among these, the "starch family", including amylose, amylopectin and dextrins, is especially preferred, but pullulan, elsinan, reuteran and other α-glucans, are also suitable, although the proportion of 1,6-linkages is preferably below 70%, more preferably below 60%. Other suitable polysaccharides include β-1,4-glucans (cellulose), β-1,3-glucans, xyloglucans, gluco-mannans, galactans and galactomannans (guar and locust bean gum), other gums including heterogeneous gums like xanthan, ghatti, carrageenans, alginates, pectin, β-2,1- and β-2,6-fructans (inulin and levan), etc. A preferred cellulose is carboxymethylcellulose (CMC, e.g. AKUCELL from AKZO Nobel).

Carbohydrates which can thus be used are carbohydrates consisting only of C, H and O atoms such as, for instance, glucose, fructose, sucrose, maltose, arabinose, mannose, galactose, lactose and oligomers and polymers of these sugars, cellulose, dextrins such as maltodextrin, agarose, amylose, amylopectin and gums, e.g. guar. Preferably, oligomeric carbohydrates with a degree of polymerization (DP) from DP2 on or polymeric carbohydrates from DP50 on are used. These can be naturally occurring polymers such as starch (amylose, amylopectin), cellulose and gums or derivates hereof which can be formed by phosphorylation or oxidation. The starch may be a cationic or anionic modified starche. Examples of suitable (modified) starches that can be modified are corn-starch, potato-starch, pee-starch, rice-starch, tapioca starch, banana starch, and manioc starch. Other polymers can also be used (e.g. caprolactone). In certain embodiments, the biopolymer is preferably a cationic starch, most preferably an oxidized starch (for instance C6 oxidized with hypochlorite). The oxidation level may be freely chosen to suit the application of the sorbent material. Very suitably, the oxidation level is between 5 and 55%, most preferably between 25 and 35%, still more preferably between 28% and 32%.

Most preferably the oxidized starch is crosslinked. A preferred crosslinking agent is di-epoxide. The crosslinking level may be freely chosen to suit the application of the sorbent material. Very suitably, the crosslinking level is between 0.1 and 25%, more preferably between 1 and 5%, and most preferably between 2.5 and 3.5%.

Proteins which can be used include albumin, ovalbumin, casein, myosin, actin, globulin, heroin, hemoglobin, myoglobin, gelatin and small peptides. In the case of proteins, proteins obtained from hydrolysates of vegetable or animal material can also be used. Particularly preferred protein polymers are gelatin or a derivative of gelatin.

Also suitable mixtures of carbohydrates (e.g. copolymers) or mixtures of proteins can be used.

In order to provide for a charged polymer, the carbohydrate polymer may for instance be modified by oxidation, substitution with cationic functional groups or with carboxymethyl groups, or by esterification with e.g. acetyl groups. Particularly preferred carbohydrate polymers are chosen from the group consisting of starch or a derivative of starch, cellulose or a derivative of cellulose, pectin or a derivative of pectin.

The formation of the matrix is accomplished through covalent cross linking of the polymers. The cross linker for crosslinking the polymers and providing the matrix structure is—in the case of carbohydrate polymers—preferably chosen from the group consisting of divinyl sulphone, epichlorohydrin, a di-epoxide such as glycerol diglycidyl ether or butanedioldiglycidyl ether, sodium trimetaphosphate and adipic acid or derivatives thereof. Typical crosslinks are ether- and/or ester-links, where for the ester-links phosphate-esters are preferable. Alternatively, the carbohydrate polymer may be cross-linked by means of a cross-linking enzyme chosen from the group consisting of peroxidases, laccases, polyphenol oxidases, transglutaminases, protein disulfide isomerases, sulfhydryl oxidases, lysyl oxidases and lipoxygenases. Methods how to use these cross-linkers or cross-linking enzymes are well known in the art.

A method for producing a polymer for use in aspects of the present invention is for instance described in EP 1 628 529 and may comprise:

a) providing a polymer (very suitably in an aqueous solution or suspension) and a cross-linker or cross-linking enzyme,
b) mixing the polymer and cross-linker or cross-linking enzyme to provide a polymer crosslinking reaction mixture;
c) activating the cross-linking by addition of base or acid to the reaction mixture;
d) allowing for cross-linking to occur and allowing gelation of the cross-linked polymer;
e) breaking the gel resulting from step d) into smaller particles; and
f) drying the polymer particles from step e) and optionally grinding these dried polymer particles into finer polymer particles.

It will be understood that the cross-linking level can be controlled by controlling the concentration of the cross-linker or the cross-linking reaction time. The level of cross-linking and the number of cross-links per polymer molecule will largely determine the pore size of the resulting polymer matrix.

The porous nature of the polymer matrix of the present invention is a key aspect. Firstly, as a result of the porous structure, fluids can enter the matrix and come into contact with (will be exposed to) the nanostructured sorption material immobilized therein. Due to this exposure, the substances of which the removal from the fluid is sought will adsorb to the nanostructured sorption material. Secondly, the porous structure of the polymer matrix will allow for the trapping of molecules of which the removal from the fluid is sought such as bilirubin. Thus, the pore size should be selected such that the entry and subsequent absorption or adsorption into the matrix of molecules whose removal from the liquid is sought is possible. Thirdly, and in contrast, the porous structure of the polymer matrix should preferably prevent the entry into the matrix of large molecules of which the removal from the fluid is not sought, such as albumin. Thus, the pore size is preferably selected such that the entry into the matrix of molecules whose removal from the liquid is not sought is impossible. The pore size is thus selected to suit the specific purification application, and may for instance be based on size exclusion of compounds of which the removal from the liquid is not sought but which should be selectively retained therein.

Since a single albumin molecule is approximately an 80 Angstrom diameter sphere, a suitable pore size for the polymer matrix in applications for blood (plasma) or dialysate purification would be less than 80 Angstrom (less than 8 nm).

Drying of the polymer particles and optional further grinding thereof into fine dried polymer particles facilitates storage capabilities of the sorbent material of the present invention. Generally a polymer particle size of 100 µm to 3000 µm (based on the size of the dried particle) is suitable. Polymer particle sizes are preferably around 200-1000 µm.

The nanostructured sorption material may be added to any of the steps a)-f) above to load the polymer particles with the nanostructured sorption material.

The advantages of cross-linked polymers lie in its intrinsic stability as a result of cross-links in the matrix. A further important advantage is that cross-linking provides a three-dimensional lattice of the cross-linked polymer, in which the nanostructured sorption material can be "filled in". Moreover, the choice of components, i.e. the choice of polymer(s) and cross-linker(s) influence the three-dimensional structure of the vehicle and thus would allow for the manufacture of specific matrices suited for retaining or excluding molecules of a certain size and/or certain charge.

The polymer matrix may be constructed from readily available and water soluble polymers such as polysaccharides and (hydrolysed) proteins and in doing so a flexible matrix may be formed and positive and/or negative charge through e.g. carboxylic acids and/or cationic groups will generate a custom made sorbent matrix. This cannot be accomplished using polysaccharides such as chitin and/or chitosan. Also the above mentioned polymers are much cheaper than the hitherto used chitin and chitosan. The possession of a charge is an important feature of a polymer for the present invention. It will greatly facilitate the formation of a complex between the nanostructured sorption material (which is often a charged molecule) and the polymer lattice. The charge can be provided by the polymer itself, but—if the polymer does not have a positive or negative charge—the charge can be introduced as a result of modification of the polymer or by the cross-linker used for cross-linking the polymer.

Modification of the polymers can be accomplished by oxidation, substitution with cationic functional groups or carbonyl and/or carboxymethyl groups and/or esterifying with e.g. acetyl groups. Although in the latter case no charge is added, it is used to make the polymer more hydrophobic to allow complexing of the polymer with nanostructured sorption materials that have little or no charge.

Generally the polymers will be modified before cross-linking and gelation. It is possible to modify the polymer after cross-linking and gelation only if cross-linking is performed by ether-formation. The person skilled in the art will know how to modify the polymers specified in the invention to provide them with the mentioned groups.

The charge of the cross-linked polymer can be negative or positive depending on the type of polymer, the type of modification and the type of cross-linking.

Advantageously, the polymers are of considerable size, i.e. 30 kD or more. This allows for the ready formation of a gel upon cross-linking and it allows for the formation of a lattice, which is capable of taking up the nanostructured sorption material.

In this way sorbent materials are formed that are stable and can be used in the various applications according to the invention. The sorbent materials will not gelate again when solved, even not when heated or boiled, and they do not spontaneous fall apart which would cause release of any nanostructured sorption material.

The size of the sorbent material particles depends on the breaking and grinding process. Breaking is preferably done by pressing the gel through a sieve of a desired mesh size. If necessary, finer particles can be formed by additional grinding the sieved particles, preferably after drying. The size of the sorbent material particles preferably can range from 0.5 µm to 1000 µm and the optimal size will depend on the specific application for which they are used. It is generally thought that small sorbent material particles are preferable for applications where contact time with the fluid from which purification is sought is short.

It is thought that loading of the nanostructured sorption materials is possible because complexes are formed due to electrostatic interactions between the charged groups of the cross-linked polymer and the charged groups on the nanostructured sorption materials. In the case that neutral components and/or polymers are used complex formation will probably be caused by hydrostatic interactions between hydrophobic groups.

In many cases, the nanostructured material will form a nanocomposite with the polymer matrix.

The selectivity of the sorbent material of the present invention can further be enhanced by loading the material with specific molecule catchers or receptors receptors such as antibodies, prosthetic groups or carboxyl groups (general: binding partners). For selective binding of proteins or degenerated proteins, antibodies are very suitable, e.g. from the immunoglobulin superfamily (IgSF), prosthetic groups e.g. from lipid and vitamin derivatives or metal ion such as gold, iron, zinc, magnesium, calcium that covalently bond to proteins, as well as carboxyl groups that can bind to proteins by forming peptide bonds.

Alternatively, the nanocomposites may comprise amorphous or crystalline Hydrated Fe Oxide (HFO). Such materials exhibit strong sorption affinity towards toxic compounds such as arsenates, arsenites, chromates, molybdates, selenites, and vanadates, but also phosphates. A very suitable material for inclusion in the sorption material of the present invention is for instance disclosed in US2005/156136. This publication is expressly referred to and incorporated herein in its entirety by reference. US2005/156136 discloses the formation of an adsorbent comprising HFO particles supported in an polymeric anion exchange material. This material is capable of selective removal of certain toxic compounds as mentioned above from a fluid stream brought into contact with the adsorbent. The particles are formed by passing a solution containing an oxidizing anion such as a permanganate, persulfate or hypochlorite, through a bed of polymeric anion exchange resin (e.g. A-500P having quaternary ammonium functional groups in chloride form). Thereafter a solution of a ferrous salt, such as ferrous sulfate, is passed through the bed, thereby simultaneously desorbing the oxidizing anion and oxidizing the ferrous ion to a ferric ion. This causes precipitation, and uniform dispersion, of a solid, hydrated ferric oxide, within the polymeric anion exchange resin. Anionic ligands such as arsenates, chromates, oxalates, phosphates, phthalates, etc., can permeate in and out of the gel phase and are not subjected to the Donnan exclusion effect. Although the polymeric matrix used in the present invention may comprise HFO particles dispersed therein (preferably hydrated Fe(III) oxides), the matrix may also comprise particles of an anion exchange matrix comprising HFO particles disperses therein (a gel matrix comprising particles in particles). The advantage of such an embodiment is that a negative charge of a gel matrix supporting nanostructured sorption materials according to the present invention that would normally repel negatively charged compounds such as arsenates and phosphates, can still support the effective removal of such compounds from a fluid feed if the HFO particles are dispersed in an anion exchange matrix.

The system of the present invention is i.a. distinguished from the prior art devices in that it makes use of nanomaterials to allow small dimensions for wearability and to allow multiple sorbent stages for removing multiple components (i.e. multiple substances from the blood), both from cationic as well as anionic nature.

The system of the present invention is also distinguished from the prior art devices in that it first separates the blood into plasma and cells/platelets. This plasma is then passed through the sorption filter where one or more additional functions are performed. Thus, a system of the present invention is capable of performing a number of functions. First, it separates blood in to plasma and cells/platelets. In addition, it absorbs the "middle molecules", such as urea, from the blood plasma via the sorption filter. Moreover, in preferred embodiments, by incorporating specific functions in the filter or other part of the device, the system is capable of performing selective sorption of viable minerals on the above mentioned sorbent materials, for instance such as to balance the mineral composition in blood. In still further embodiments, the system is capable of supplying specific components to the blood plasma. These components may be supplied from separate containers or, and preferably, they may be supplied via the incorporation of slow release systems, which are per se known to the skilled person, in the sorption filter system. The additional components may for instance include such ingredients as calcium, vitamin A, anti-coagulation agents, anti microbial agents, minerals, specific medicaments etc.

The selectivity of the absorption, adsorption, ion-exchange and/or surface crystallisation material can further be enhanced by loading the material with specific molecule catchers or receptors. For selective absorption of proteins or degenerated proteins, antibodies can be used, e.g. from the immunoglobulin superfamily (IgSF), prosthetic groups e.g. from lipid and vitamin derivates or metal-ions such as gold, iron, zinc, magnesium, calcium that covalently bind to proteins as well as carboxyl groups that can bind proteins by forming peptide bonds. Such selective absorbing agents can further enhance the selectivity of the filter pad for toxic proteins.

In a preferred embodiment, the device of the present invention comprises means for regulating the content of minerals and other substances in the blood plasma via selective sorption and controlled release.

In a preferred embodiment therefore, the device for the removal of toxic substances from blood from a patient, comprises a hemofilter and a sorption-filter, wherein the sorption filter removes small and middle-sized molecules from the blood based on the plasma, and includes such functions as selective sorption, controlled release and anti-microbial control.

In a most preferred embodiment, the hemofilter and sorption-filter are comprised in a single part. For instance, the hemofilter may enclose the sorbent material, so as to form a filter pad, wherein the envelop of the pad is formed by the hemofilter material, and the contents of the pad are formed by the sorbent material. The general design of such pads is well known in coffee-machines, such as the Senseo® system. This type of filtering pad (pill-shaped pouch) will allow simple inclusion of materials for (slow) release of additional components or additional (an)ion exchange systems. In this form it is referred to herein as a sorption and release system.

To accommodate the fitting of a filtering pad, comprising a hemofilter envelop and an sorbent material content, the device of the invention may suitably comprise a filter pad holder, designed to receive the filtering pad and provide for a fluid-flow from across the filter pad, in particular a blood flow, so that blood reaching the filter pad is separated into cells and plasma, plasma passing through the part of the filter that holds the absorbent material, and purified and optionally supplemented blood plasma exits the filter pad and exits the filter pad holder. Thus, in such an embodiment, the inlet for receiving blood from a patient, and the outlet for recovery of purified blood plasma, are present, while outlet for recovery of patient blood plasma and inlet for receiving patient blood plasma exiting said hemofilter, are absent.

It will be understood that the advantage of such a filter pad is that it forms a disposable and replacement part of the device, and can be replaced by a fresh filter pad, for instance when it has been saturated with toxic substances, or if one or more of the components supplemented to the plasma have run out. The sorption capacity of the filter pad for urea and the middle molecules is typically in the range of 30-70% of its own weight, but can reach 100% for specific molecules.

The device of the present invention can be used for filtering or purification of blood of patients with a (developing) renal failure. In a preferred embodiment, the device takes the form of a wearable artificial kidney device, but can also be embodied in desktop sized equipment or in adapted hemodialysis or peritoneal dialysis equipment.

The artificial kidney is able to perform some of the functions which normally will be done by a properly functioning human or animal kidney, in particular filtering of blood and regulation and control of the content of substances in the blood. The device of the present invention comprises an sorption system for capturing toxic substances from the blood and optionally a release system for releasing minerals, vitamins or other substances to the blood, a filter for separating blood cells from blood plasma on the basis of hemofilter having micron-sized pores (min. 2 microns up to 20-30 microns) a vascular access and feedback system for attachment to a body, sensors (connection of filter pad, flow, temperature, anti-coagulation, ion-selective or small and middle-sized molecule selective sensors), a (micro)fluidic circuitry including flow restrictions, pump(s) and tubing, a preferably wireless uplink (wireless radio sensor) to a computer of the care giver or doctor located elsewhere (ZigBee, DECT, GSM/GPRS, Bluetooth or other), an anti-microbial control system consisting of embodied anti-microbial materials in the disposable parts of the system (tubing, vascular access, filter cartridge), a basic user interface for the patient to indicate proper working of the devices, a battery and a PCB with a DSP, inputs and outputs to the sensors, user interface, an integrated blood pressure sensor in the device etc.

The sorption and release system has a temporary use till it reaches its maximum capacity. The content of the sorption and release system can be customized to the individual patient needs.

The invention claimed is:

1. A device for the removal of toxic substances from dialysate fluid, blood or blood plasma, said device comprising:
   i) a sorption filter for removing toxins, toxic solutes, toxic small and middle-sized molecules and protein bound toxins from the dialysate fluid, blood or blood plasma, said sorption filter comprising a nanostructured sorption material made of nanoparticles or nanocrystalline materials captured in a porous polymer matrix, wherein the pores in said porous polymer matrix are of a size that allows the entry into said matrix of substances sought to be removed from said liquid while preventing the escape of said nanostructured sorption material and/or preventing the entry into said matrix of substances not sought to be removed from said liquid; said sorption filter being contained in a housing;
   ii) an inlet for entry of said dialysate fluid, blood or blood plasma into said device;
   iii) an outlet for the removal of purified dialysate fluid, blood or blood plasma from said device, and
   iv) a conduit connecting said inlet with said outlet and holding said sorption filter such that said dialysate fluid, blood or blood plasma must pass through said sorption filter when flowing from said inlet to said outlet.

2. Device according to claim 1 wherein said porous polymer matrix is based on a cross-linked polymer and/or a charged polymer.

3. Device according to claim 2, wherein said cross-linked polymer and/or a charged polymer is a biopolymer selected from carbohydrates and proteins.

4. Device according to claim 3, wherein said carbohydrate is selected from an oxidized crosslinked starch and a carboxymethyl cellulose.

5. Device according to claim 1 wherein the pores in said matrix are of a size that prevents the entry into said matrix of albumin.

6. Device according to claim 1, wherein said toxic substances are selected from potassium, phosphate, urea, uric acid, ammonia, creatinine, beta2-microglobulin ($\beta 2M$), and albumin-bound toxins.

7. Device according to claim 1, wherein said sorbent material further comprises means for supplementing said dialysate fluid and/or said optionally purified blood plasma with at least one substance selected from vitamins, minerals, anticoagulants, anti microbial agents and medicaments.

8. Device according to claim 1, wherein the sorbent material is provided in the form of dried granules having a mean size over the range 250 microns to 1500 microns based on the size in dried form.

9. Device according to claim 1, wherein said sorption filter is provided in the form of a filter pad comprising the sorbent material.

10. Device according to claim 1, wherein said device further comprises means for supplementing said dialysate fluid and/or said blood plasma and/or said purified blood plasma with at least one substance selected from vitamins, minerals, anticoagulants, anti microbial agents and other medicaments.

11. Device according to claim 1, wherein said device further comprises a pump for pumping said dialysate fluid, blood or blood plasma from said inlet to said outlet.

12. Device according to claim 1, wherein said sorption filter is combined with a hemofilter system in order to form an artifical kidney device for the removal of toxic substances from the blood of a patient, comprising a hemofilter for separating patient blood plasma from patient blood cells.

13. Device according to claim 12, wherein said artificial kidney system is a wearable device.

14. Device according to claim 13, wherein said hemofilter comprises at least one inlet for receiving blood from a patient, and at least one outlet for recovery of patient blood plasma.

15. Device according to claim 14, wherein said hemofilter comprises at least a further outlet for recovery of patient blood cells.

16. Device according to claim 12, wherein said sorption filter comprises an inlet for receiving patient blood plasma exiting said hemofilter, and at least one outlet for recovery of purified blood plasma.

17. Device according to claim 12, wherein said sorption-filter is combined with a permeable envelop to form a filter pad comprising an envelope surrounding contents of the filter pad, wherein the envelope of said pad comprises a permeable membrane and the contents of said pad comprise said sorbent material.

18. Device according to claim 12, wherein said hemofilter and said sorption filter are combined to form a filter pad comprising an envelope surrounding a filter pad contents, wherein the envelope of said pad comprises said hemofilter, and the contents of said pad comprise said sorbent material.

19. Device according to claim 1, wherein said device further comprises ion exchange systems.

20. Device according to claim 1, wherein said device further comprises surface crystallisation systems.

21. Filter pad comprising a sorbent material adapted for being held in a conduit,
   wherein said sorbent material is a nanostructured sorption material made of nanoparticles or nanocrystalline materials captured in a porous polymer matrix, wherein the pores in said porous polymer matrix are of a size that allows the entry into said matrix of substances sought to be removed from said liquid while preventing the escape of said nanostructured sorption material and/or preventing the entry into said matrix of substances not sought to be removed from said liquid; said sorption filter being contained in a housing, and
   wherein said conduit connects said inlet with said outlet and holding said sorption filter such that said dialysate fluid, blood or blood plasma must pass through said sorption filter when flowing from said inlet to said outlet.

22. Filter pad according to claim 21, wherein the sorbent material is provided in the form of dried granules having a mean size over the range 250 microns to 1500 microns based on the size in dried form, and further comprising a permeable envelope containing said sorbent material.

23. Device according to claim 1, wherein said nanoparticles or nanocrystalline materials are selected from metal silicates, metal hydroxides, and pure metaloxide nanoparticles.

24. Device according to claim 23, wherein said metal silicates are selected from nanoclays and exfoliated nanoclays.

25. Device according to claim 23, wherein said metal hydroxides are selected from double layered hydroxides.

26. Device according to claim 25, where said metal hydroxides are selected from nano-hydrotalcite.

27. Device according to claim 23, wherein said nanoporous materials are selected from zeolites, mesoporous systems, and metal organic frameworks.

28. Device according to claim 6, wherein the albumin-bound toxins are selected from bilirubin and paramino hippuric acid.

29. Device according to claim 9, wherein the device further comprises a hemofilter.

30. Device according to claim 12, wherein the sorption filter supplements the blood with at least one substance selected from vitamins, minerals, anticoagulants, anti microbial agents and other medicaments.

31. A wearable dialysis system comprising a sorption filter comprising a nanostructured sorption material captured in a porous polymer matrix, wherein pores in said porous polymer matrix are of a size that allows entry into said matrix of substances sought to be removed from a liquid while preventing the escape of said nanostructured sorption material and/or preventing the entry into said matrix of substances not sought to be removed from said liquid, wherein said sorption filter is part of a hemodialysis or peritoneal dialysis system.

* * * * *